(12) United States Patent
Ehrick

(10) Patent No.: US 7,471,383 B2
(45) Date of Patent: Dec. 30, 2008

(54) METHOD OF AUTOMATED QUANTITATIVE ANALYSIS OF DISTORTION IN SHAPED VEHICLE GLASS BY REFLECTED OPTICAL IMAGING

(75) Inventor: Michael R. Ehrick, Toledo, OH (US)

(73) Assignee: Pilkington North America, Inc., Toledo, OH (US)

( * ) Notice: Subject to any disclaimer, the term of this patent is extended or adjusted under 35 U.S.C. 154(b) by 0 days.

(21) Appl. No.: 12/002,019

(22) Filed: Dec. 14, 2007

(65) Prior Publication Data

US 2008/0144044 A1 Jun. 19, 2008

Related U.S. Application Data

(60) Provisional application No. 60/875,725, filed on Dec. 19, 2006.

(51) Int. Cl.
*G01N 21/00* (2006.01)
(52) U.S. Cl. .................................... 356/239.1
(58) Field of Classification Search ................ None
See application file for complete search history.

(56) References Cited

U.S. PATENT DOCUMENTS

| 2,902,898 | A | | 9/1959 | Kops |
| 5,367,378 | A | | 11/1994 | Harding |
| 6,100,990 | A | | 8/2000 | Ladewski |
| 6,392,754 | B1 | * | 5/2002 | Pingel et al. ................ 356/603 |

* cited by examiner

*Primary Examiner*—Michael P Stafira
(74) *Attorney, Agent, or Firm*—Marshall & Melhorn, LLC

(57) ABSTRACT

The present application describes and claims an opto-electronic method of quantitatively analyzing reflected optical distortion in sheets or panels of shaped glass.

9 Claims, 3 Drawing Sheets

METHOD OF AUTOMATED QUANTITATIVE ANALYSIS OF DISTORTION IN SHAPED VEHICLE GLASS BY REFLECTED OPTICAL IMAGING

RELATED APPLICATION

This application is claiming the benefit under 35 USC §119(e), of the provisional application filed Dec. 19, 2006 under 35 USC §111(b) which was granted Ser. No. 60/875, 725. This provisional application is hereby incorporated by reference.

BACKGROUND

The present invention relates to an opto-electronic method of analyzing distortion in a piece of shaped glass in an objective, quantitive way that is nonetheless representative of visual human assessment of such distortion.

Detection of defects in commercially produced flat glass has always been critical in the flat glass industry. High volume production of flat glass by the float process has required detection of defects very quickly, as the continuous ribbon of glass is moving past a given stationary point at a speed of hundreds of inches per minute. Human visual assessment and automated systems have both been used to detect glass defects in float glass production processes, with visual human assessment often being as reliable, or more reliable, than automated systems, due to the large number of variables which can affect a rapidly moving ribbon of glass.

Often, such float glass is further processed, for example, to shape a glass sheet or panel for use as a vehicle glazing. Glass shaping processes, typically, involve reheating the glass sheet or panel to, or near, its softening temperature, and then shaping the glass by, for example, gravity bending or press bending. Such heating and shaping operations have the potential to create new kinds of defects in the glass sheet or panel, for example optical distortion. As with the float glass production process defects, visual human assessment has most often been the most effective way of judging the acceptability of optical distortion in shaped glass sheets or panels. Visual human assessment is necessarily, however, subjective, and quantification of distortion by such assessment methods, unreliable. Efforts to date to develop an automated system of assessment of optical distortion in shaped glass, at least by utilization of reflected light have been, largely, unsuccessful, due as in the case of assessing defects in the case of float glass production, to the large number of variables which must be taken into account. It would be desirable to have an automated system to quantitatively assess optical distortion in shaped glass sheets or panels, by use of a method which closely approximates human visual assessment, that is, by viewing a reflected optical image.

Automated systems purported to detect and measure defects in shaped glass sheets or panels are the subject of many U.S. patents. For example:

U.S. Pat. No. 4,853,777 describes a system to quantitatively determine the short-term and long-term waviness of a smooth surface by impinging light radiation, namely laser light, onto the surface, detecting the resultant light image and mathematically processing the subject light image.

U.S. Pat. Nos. 6,376,829 and 6,433,353 describe a method and apparatus for detecting front surface irregularities in a glass plate. More specifically, the method described involves irradiating a beam of light toward a surface of a transparent plate at an angle of incidence between 86° and 89°, or 60° to 89° after such light beam is polarized ("P" or "S"-polarized) by a polarizing element between the light beam source and the transparent plate. A reflected image from a front surface of the transparent plate is then projected on a screen, is inspected by one of several possible methods, whereby density signals said to be representative of the reflected image are analyzed to calculate the irregularities present on the surface of the transparent plate.

U.S. Pat. No. 6,100,990 describes a method of determining reflective optical quality of a reflective product including reflecting a first gray scale pattern off the product; obtaining a first image of the first pattern with an image pickup device after the first pattern has reflected off the product; and determining optical quality of the product based on data obtained from the first image.

U.S. Patent Application Publication No. US2006/0050284A1 describes a process for scanning a surface of a substrate, which process consists in taking at least one reflected image of at least one test pattern on the substrate surface and extracting by digital processing, local phases in two directions. Variations in local slopes are calculated by digital processing from the local phases in order to deduce therefrom variations in curvature or variations in altitude of the substrate surface.

JP61223605A describes a method for inspecting the surface shape of an object by illuminating a specular surface and an inspecting plate by a light source which is arranged above the object to be inspected. Lines are recorded at a certain pitch on the lower face of the object. The light from the plate is made incident on the surface of the object through optical path A. The light from the plate is reflected on the surface of the object and follows optical path B to reach a lens. The lens forms the image of the stripe pattern recorded on the plate on the image receiving face of an image pickup device. The image pickup device converts this image to a video signal and sends it to a picture display device and a picture process or the strip pattern for the flat surface is stored in the processor, and this pattern is compared with the inputted stripe pattern, and the substrate surface is judged to be rugged if the patterns are different from each other.

WO99/34301 describes a three dimensional surface contouring method based on the full-field fringe projection technique. More particularly, a digital video projection system is used to project digitally created fringe patterns onto an object. The fringe pattern as distorted by the geometry of the object surface is then captured by a high resolution CCD camera. To increase contouring resolution, purely software-based digital phase shifting technique is used, which is said to eliminate the need for accurate positioning systems in the traditional phase shifting methods. The surface is reconstructed by applying phase wrapping and unwrapping algorithms.

SUMMARY OF THE INVENTION

The present invention is directed to a method of quantitatively analyzing reflected optical distortion in shaped automotive glass sheets or panels and doing so in a manner which allows correlation of the analysis of individual glass sheets or panels to effect changes in, for example, a glass shaping production process.

The method of the present invention utilizes a visible light source to illuminate an essentially vertical flat, rigid surface having a repetitive pattern disposed thereon, for example, alternating dark and light stripes. The light from the visible light source is reflected from the vertical, rigid patterned surface onto a pre-positioned, essentially horizontal surface, on which a shaped glass sheet or panel, convex side facing outward, has been precisely oriented in order to highlight an area of the glass sheet where optical distortion is suspected. The pattern reflected from the illuminated vertical, rigid patterned surface is then visible in reflection on a major surface of the shaped glass sheet. The image of the pattern visible on the surface of the shaped glass sheet is reflected to a pre-positioned opto-electronic device, for example, a digital camera, which captures the image, digitally, for transfer to a computer containing at least one algorithm capable of analyzing the digital image transferred from the opto-electronic device. The at least one algorithm computes the maximum percent change in apparent variation in a contiguous group of a predetermined number of the shapes of the repetitive pattern disposed on the vertical flat surface in the area selected for analysis.

BRIEF DESCRIPTION OF THE DRAWINGS

Other features and advantages of the invention will be readily apparent from the following detailed description when taken in conjunction with the accompanying drawings.

DETAILED DESCRIPTION OF THE INVENTION

The present invention is directed to a method of quantitatively analyzing optical distortion in shaped automotive glass, particularly, where such analysis is done repeatedly in, for example, a glass quality assessment laboratory, or directly as a component of a glass shaping production process. The method of the present invention is implemented by utilizing a number of components integrated into an effective, yet relatively simple system.

Discernment of reflected distortion depends not only on the shape uniformity of the reflecting (window) surface, but also on the relative positions of the viewer/observer, the reflecting surface and the reflected patterned background. For example, surface shape irregularities that produce unacceptable distortion in a given orientation may be virtually unnoticeable if rotated 90 degrees from that given orientation. The present invention utilizes the above-noted principles to simulate real-world viewing geometry, and directly measures reflected distortion, as perceived by a viewer/observer in that geometry.

Figure 1:
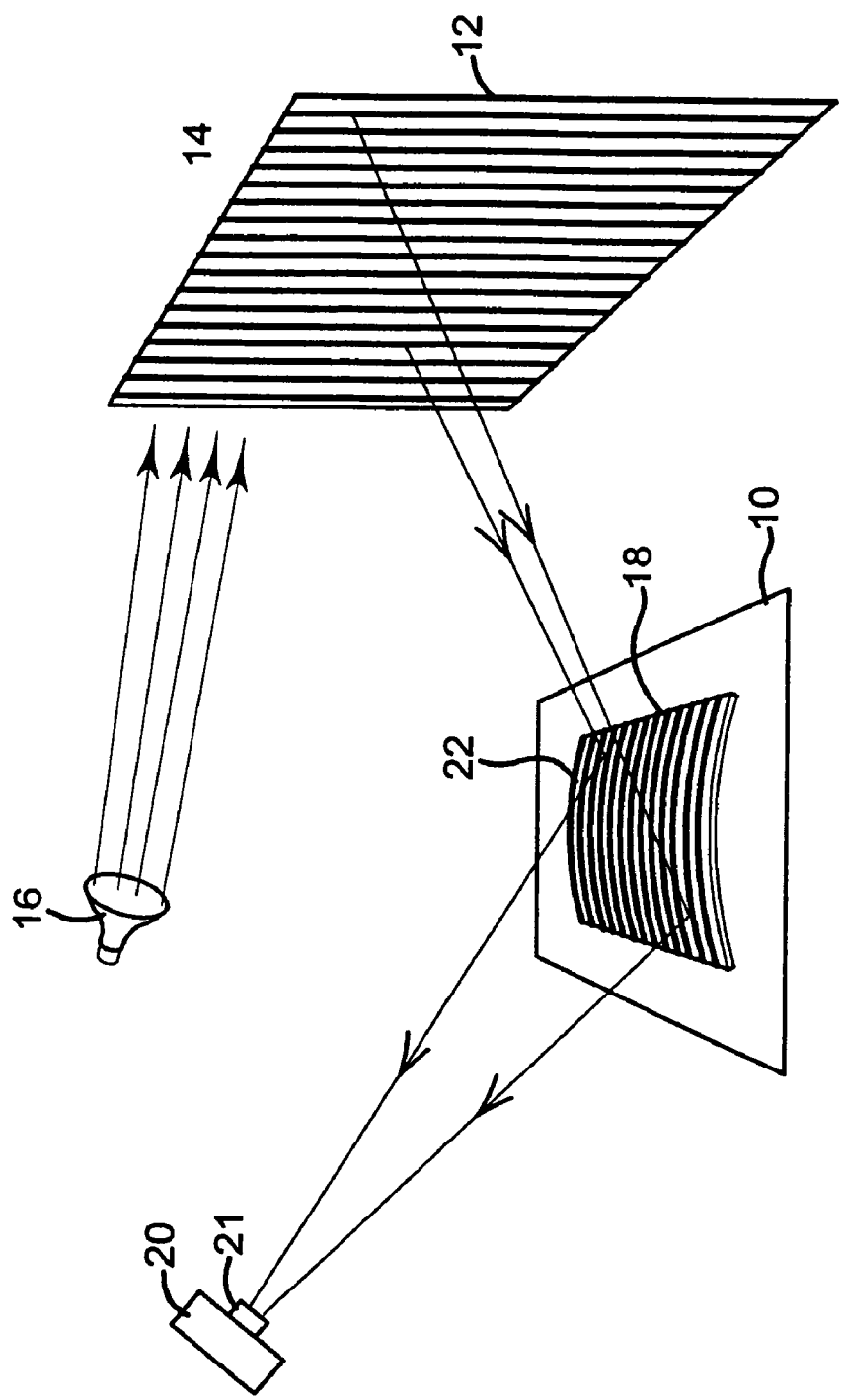
FIG. 1 shows a schematic representation of the imaging/analytical system of the present invention.

As shown in FIG. 1, a rigid horizontal surface 10, such as a registration table, or a surface in a glass sheet transport system, is placed in predetermined proximity to an essentially vertical, flat, rigid surface 12, preferably with a repetitive pattern 14 disposed thereon. While any suitable pattern may be utilized, a pattern of alternating light and dark stripes is preferred. While not critical, the typical size of the subject horizontal and vertical surfaces are 48 in.×60 in. and 72 in.×72 in., respectively. A source of visible light 16 is positioned in predetermined proximity to the essentially vertical, flat, rigid surface 12, typically within 8-10 feet of the vertical surface 12. The source of visible light 16 may be any suitable source, but may preferably be one or more incandescent flood lamps each having an output of, for example, 250 watts (3600 lumens). The light 16 is shown on the patterned vertical, flat, rigid surface 12 and is reflected diffusely therefrom onto the horizontal rigid surface 10. The vertical, flat, rigid surface 12 could also be lighted from behind the surface with, for example, opaque black stripes alternating with translucent white stripes.

A shaped sheet or panel of glass 18, convex side facing outward, is precisely oriented on the rigid horizontal surface 10 with respect to the patterned, vertical flat surface 12, as shown in FIG. 1. The precise orientation may be accomplished by rotating the glass sheet or panel on the rigid horizontal surface 10 until the reflected image has discernible, but not chaotic displacement of the reflected pattern. In a preferred orientation, the glass surface irregularities of concern are perpendicular to the "line of sight" of the image capture device 20. Such orientation is necessary for each different type of glass sheet or panel in order to optimally identify features of interest in a selected area of the convex surface of the shaped glass sheet. Less than optimal orientation could complicate the analysis of the pattern, perhaps, in some cases, beyond the capability of the analytical portion of the system and to simulate the real-world viewing geometry in which the features are objectionable. Upon proper orientation, the pattern on the patterned, vertical, surface 12 is reflected onto a major surface 22 of the glass sheet or panel 18. The reflected image of the pattern from the vertical, surface 12 visible on the major convex surface 22 of the shaped glass sheet 18 (the upper or outer surface), is altered by the curvature of the shaped glass sheet. Reflected optical distortion, if any, will also be visible, as a skewing of the lines of the reflected pattern. The light beams forming the visible image of the pattern on the glass sheet are, primarily, reflected into the image capture portion 24 of an opto-electronic device at an angle of incidence of between 15° and 45° below the horizontal. The image capture portion 24 may be the lens of, for example, a digital camera. Other suitable image capture devices 20 could include an analog video camera. The image captured is digitized in the image capture device 20 or another device, and is transmitted by known methods to a suitable computer (not shown). Typically, the image capture device 20 will be positioned so as to receive an optimal amount of the light reflected uniformly from the surface 22 of the shaped glass sheet 18, as shown in FIG. 1. The distance between the shaped glass sheet 18 and the image capture device 20 is preferably 4-12 feet, most preferably between 8 feet and 10 feet. The axis angle of the image capture portion 24 of the image capture device 20 should be set so as to be compatible with the angle of incidence of the light reflected from the shaped glass sheet 18.

Figure 2:
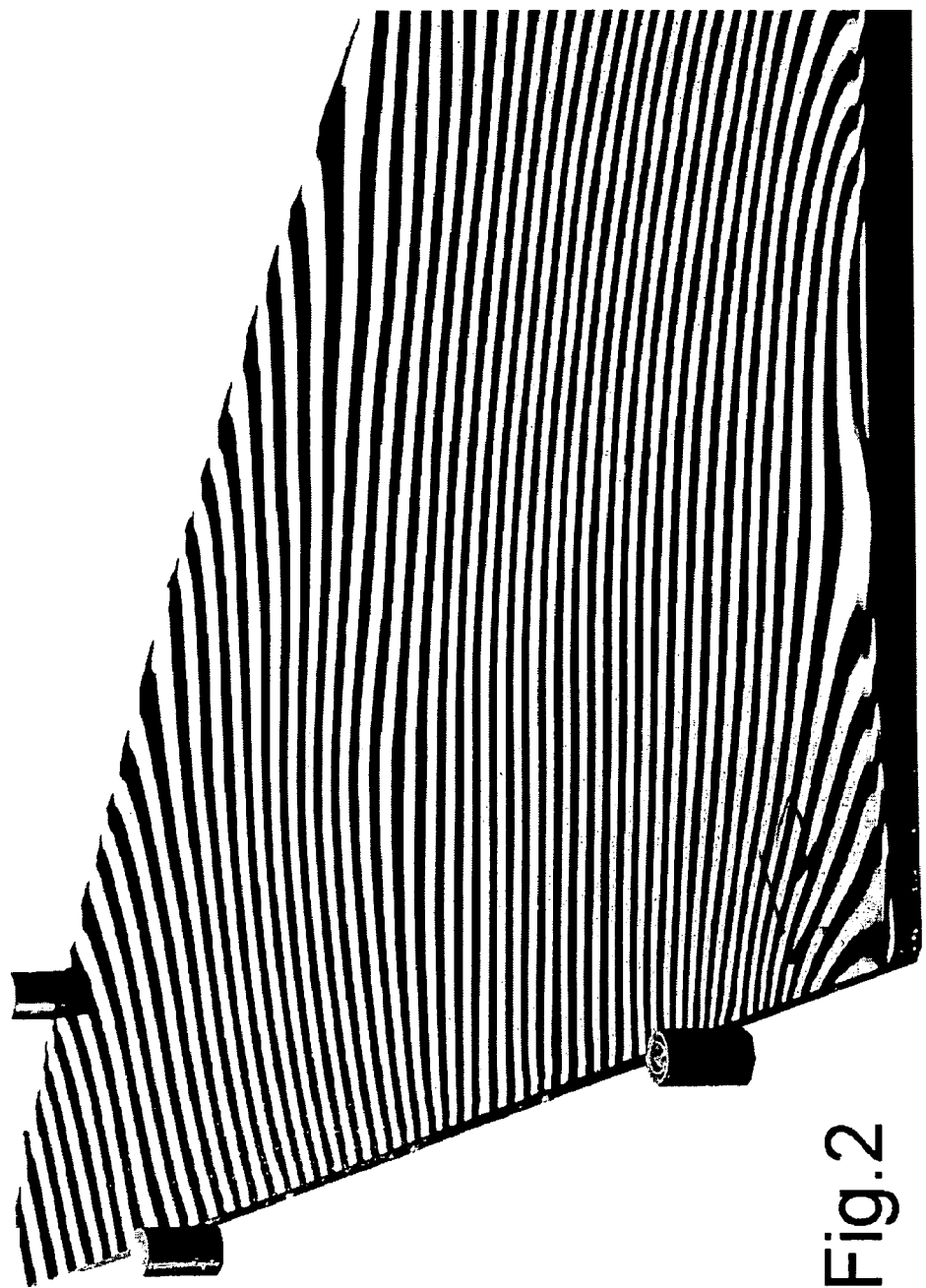
FIG. 2 is a photograph of a representative glass panel exhibiting a reflected pattern which shows some level of distortion in the panel.
Figure 3:
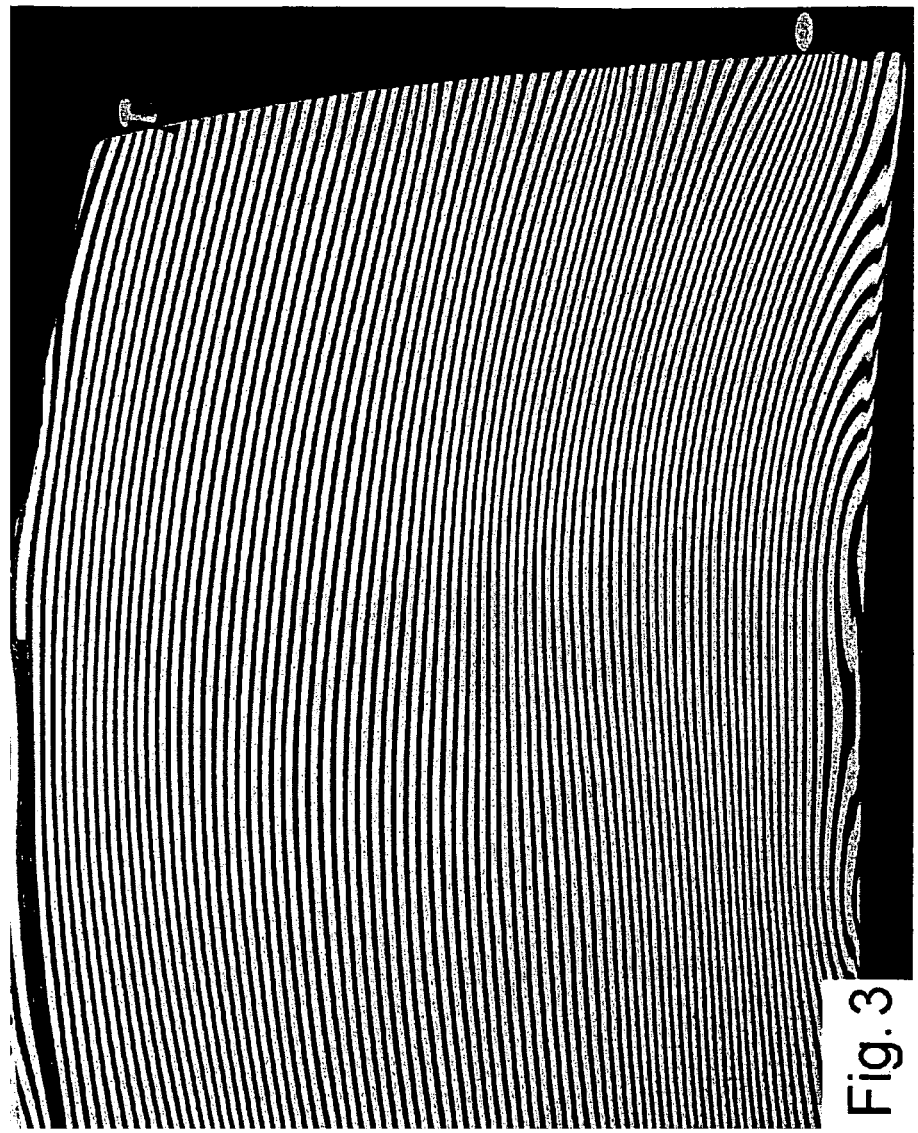
FIG. 3 is a photograph of a representative glass panel exhibiting a reflected pattern which shows negligible distortion in the panel.

The digital image data transmitted to the computer is analyzed by at least one algorithm to quantify reflected optical distortion present in the selected area of the shaped glass sheet 18. The at least one algorithm computes the maximum percent change in apparent variation in a contiguous group of a predetermined number of the shapes of the repetitive pattern disposed on the vertical flat surface in the area selected for analysis. In a preferred embodiment, the algorithm computes the maximum percent change in apparent stripe width across a group of, for example, eight contiguous stripes, as illustrated in FIG. 2. This algorithm may be utilized to analyze areas on the glass sheet 18 where, for example, a change in the width of the stripe is identified by a human observer. Other potentially useful algorithms base computations on changes in the orientation, slope or curvature of stripe edges.

Generally, the method of the present invention is advantageous in that "second surface" reflection (i.e., reflection of light from the major concave surface of the shaped glass sheet) is minimized to an extent that it does not significantly interfere with the analysis of the convex major surface of the glass sheet. This is so because the image analysis algorithm has been specifically designed to handle the superposition of images reflected from the first and second surfaces of the shaped glass sheet. Such double reflections are especially problematic with light-colored glass compositions where attenuation of the second surface reflection is minimal.

It is anticipated that the present invention will have particular applicability for vehicle sidelights and sunroofs, and, at least, the less curved portions of vehicle backlights. Qualitative correlation, more particularly, rank order correlation, of the system of the present invention to visual assessment of distortion by an experienced human observer has been shown to be excellent.

Those skilled in the art of analysis of glass distortion will appreciate that those defects made evident by reflected light are different from defects exposed by use of transmitted light shown through a glass pane. In particular, distortion in glass disclosed by the use of reflected light may be caused by small irregularities in surface curvature made most evident when viewed along, for example, a vehicle window at a low angle of incidence. Such defects in the appearance of the exterior of vehicle glass are of increasing concern, especially, to some manufacturers of luxury and near-luxury vehicles.

The present invention has been described in an illustrative manner. Many modifications and variations of the present invention will occur to those skilled in the art of shaped glass analysis in light of the teachings herein. Therefore, applicants submit that within the scope of the appended claims, the present invention may be practiced otherwise than as specifically described.

What is claimed is:

1. A method of quantitatively analyzing optical distortion in shaped glass comprising:
   providing a rigid horizontal surface on which to position a shaped sheet of glass;
   positioning a flat rigid surface in an essentially vertical orientation and in a predetermined proximity to the horizontal surface on which the shaped glass is to be positioned, the vertical flat surface having a repetitive pattern disposed thereon;
   providing at least one source of visible light to illuminate the vertical, rigid patterned surface;
   providing an optoelectronic device capable of receiving and recording a digital image, which optoelectronic device is positioned in a predetermined proximity to the rigid horizontal surface and to the flat, patterned vertical surface;
   providing a computer programmed with at least one algorithm capable of receiving a digitized image from the optoelectronic device;
   precisely orienting a shaped sheet of glass having at least one major convex surface on the rigid horizontal surface relative to the vertical, rigid flat surface;
   selecting an area of the at least one major convex surface for analysis;
   utilizing the optoelectronic device to capture a digital image of the pattern formed on the shaped sheet of glass by the light reflected to the optoelectronic device from the patterned vertical rigid surface; and
   electronically transferring the digital image of the pattern on the surface of the shaped glass sheet to the computer, wherein the at least one algorithm computes the maximum percent change in apparent variation in a contiguous group of a predetermined number of the shapes of the repetitive pattern disposed on the vertical flat surface in the area selected for analysis.

2. The method defined in claim 1, wherein the optoelectronic device is a digital camera.

3. The method defined in claim 1, wherein the pattern displayed on the essentially vertical flat surface is a repetitive linear pattern.

4. The method defined in claim 2, wherein the pattern displayed on the essentially vertical flat surface is a series of alternating light and dark, parallel stripes.

5. The method defined in claim 1, wherein the horizontal surface is a transport system capable of transporting a plurality of shaped glass sheets in serial fashion such that the digital image of each glass sheet is captured and analyzed.

6. The method defined in claim 4, wherein the at least one algorithm computes the maximum percent change in apparent stripe width across a group of a predetermined number of contiguous stripes.

7. The method defined in claim 6, wherein a second algorithm computes changes in the orientation, slope or curvature of stripe edges.

8. The method defined in claim 1, wherein the shaped glass sheet is oriented so that glass surface irregularities of concern are perpendicular to the line of sight of the image capture device.

9. The method defined in claim 1, wherein the light beams reflected from the surface of the shaped glass sheet are substantially reflected into the image capture portion of an optoelectronic device at an angle of incidence between 15° and 45° below the horizontal.

* * * * *